United States Patent

Driver

[11] 4,041,941
[45] Aug. 16, 1977

[54] MEANS FOR AND METHOD OF REMOVING A CAST

[76] Inventor: K. Dwight Driver, 5338 Patrick Henry, Bartlett, Tenn. 38134

[21] Appl. No.: 683,315

[22] Filed: May 5, 1976

[51] Int. Cl.$^2$ .................... A61F 15/02; A61F 13/04
[52] U.S. Cl. .............................. 128/91 A; 30/166 R; 145/31 R
[58] Field of Search .................. 128/91 A, 83, 317; 30/166 R; 145/31 R

[56] References Cited

U.S. PATENT DOCUMENTS

| 2,206,339 | 7/1940 | Ulman | 128/91 A |
| 2,837,088 | 6/1958 | Moses | 128/91 A |

FOREIGN PATENT DOCUMENTS

| 72,145 | 7/1916 | Austria | 128/91 A |
| 1,148,624 | 6/1957 | France | 128/91 A |
| 278,766 | 2/1952 | Switzerland | 128/91 A |
| 702,121 | 1/1954 | United Kingdom | 128/91 A |

Primary Examiner—Ronald L. Frinks

Attorney, Agent, or Firm—John R. Walker, III

[57] ABSTRACT

A device for and a method of removing a cast from a body member. A flexible elongated strip member is attached to the body member before the cast is applied thereto. The strip member is provided with an elongated aperture along the longitudinal axis thereof. When it is desired to remove the cast, the first end of a flexible elongated saw member is inserted through the elongated aperture in the strip member until a portion of the first end of the saw member extends past the strip member. The first end of the saw member is smooth while the second end thereof includes a plurality of saw teeth mounted thereon and includes a handle member fixedly attached thereto. After the first end of the saw member is inserted through the elongated aperture in the strip member, a handle member is attached to the portion of the smooth first end of the saw member that extends past the strip member. The saw member is then moved back and forth within the elongated aperture in the strip member to cut through the cast.

10 Claims, 11 Drawing Figures

MEANS FOR AND METHOD OF REMOVING A CAST

BACKGROUND OF THE INVENTION

1. Field of the Invention

This invention relates generally to devices for and methods of removing casts from body members and more specifically to such devices and methods that utilize an elongated saw member to remove the cast.

2. Description of the Prior Art

Heretofore, various devices for and methods of removing casts from body members have been developed. For example, power saws having rotating or oscillating blades have been used to remove casts from body members. Such power saws have not proved entirely satisfactory for a number of reasons. More specifically, such power saws frequently cause great trauma to the patient having the cast removed from his body member because of the proximity of the rotating or oscillating blade to the patient and because of the loud noise made as the saw cuts through the cast. This disadvantage is particularly noticeable when the patient is a child or the like. Also, such power saws are not as efficient as desired because of the need to cut entirely through the cast to allow the cast to be removed while taking care not to touch the patient's body member with the rotating or oscillating blade. This requires the person cutting the cast with the power saw to proceed slowly and carefully and, therefore, less efficiently with the cutting operation.

Another device for and method of removing casts from body members utilizes an elongated wire imbedded in the cast and a mechanical apparatus for applying a sufficient tension force to body ends of the elongated wire to pull the elongated wire through the cast. Such a device has not gained wide acceptance because of the possibility of pain and injury to the patient when the elongated wire is pulled through the cast.

Another device for and method of removing casts from body members utilizes an elongated flexible saw to manually cut through the cast. Such elongated flexible saws include a plurality of saw teeth along their entire length and are normally placed within a metal trough or the like that is imbedded in the cast with the bottom of the trough against the patient's body member whereby back and forth manual movement will cause the saw to cut through the cast while the metal trough prevents the saw from cutting the patient. While such elongated flexible saws overcome many of the problems heretofore discussed relative to other devices for and methods of removing casts from body members, they have not provided entirely satisfactory. For example, the metal troughs of such elongated flexible saws do not easily conform to the shape of the body member to which the cast is being applied. None of the above devices for and methods of removing casts from body members discloses or suggests the present invention.

SUMMARY OF THE INVENTION

The present invention is directed towards overcoming the problems and disadvantages of prior devices for and methods of removing casts from body members. The concept of the present invention is to provide means which allows a cut to be quickly made through a cast without danger of injury to the patient and without causing the patient to become uneasy. This means includes a flexible elongated saw member having a plurality of saw teeth mounted on one end thereof with the other end being smooth. A first handle member is removably attached to the smooth end of the saw member and a second handle member is fixedly attached to the other end thereof. Preferably, a flexible elongated strip member having an elongated aperture along the longitudinal axis thereof is attached to the body member before the cast is applied thereto.

To remove a cast from a body member utilizing the present invention, the smooth end of the saw member is inserted through the elongated aperture in the strip member so that a portion of the smooth end thereof extends past the strip member. The first handle member is then attached to the portion of the smooth end of the saw member that extends past the strip member and the saw member is moved back and forth within the elongated aperture in the strip member by alternately pulling and relinquishing alternate ones of the handle members thereby causing the plurality of saw teeth of the saw member to cut through the cast.

DESCRIPTION OF THE PREFERRED EMBODIMENT

Figure 1:
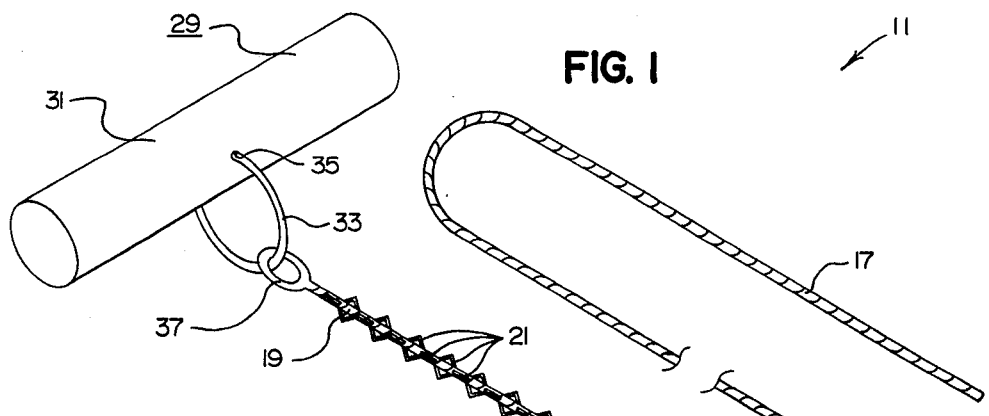
FIG. 1 is a perspective view of the flexible saw member of the saw means of the present invention.
Figure 2:
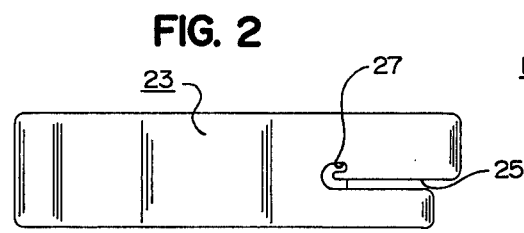
FIG. 2 is a top view of the removable handle member of the saw means of the present invention.
Figure 3:
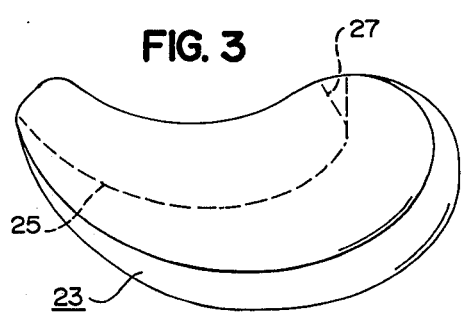
FIG. 3 is a front view of the removable handle member of the saw means of the present invention.
Figure 4:
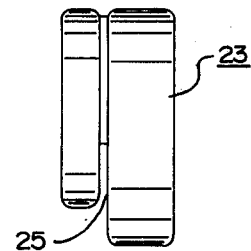
FIG. 4 is an end view of the removable handle member of the saw means of the present invention.

The means for and method of removing a cast from a body member of the present invention is especially adapted for use in orthopedic procedures in which a cast is applied to the body member of a patient to correct or cure injuries or deformities in the skeletal structure of the patient's body member. In general, the means for removing a cast from a body member of the present invention includes a saw means 11 for cutting through the cast. Preferably, the means for removing a cast of the present invention also includes a guide means 14 for guiding the saw means 11 as the saw means 11 cuts through the cast.

The saw means 11 includes a flexible elongated saw member 15 having a first end 17 and a second end 19. The first end 17 of the saw member 15 is smooth while the second end 19 of the saw member 15 includes a plurality of saw teeth 21. The plurality of saw teeth 21 may be constructed in any manner well known to those skilled in the art. Preferably, the saw member 15 is constructed of woven wire and the plurality of saw teeth 21 are formed by varying the pitch of alternating strands of the woven wire in a manner which should be apparent to those skilled in the art. The saw means 11 also includes a first handle member 23 for being removably attached to the smooth first end 17 of the saw member 15 in any number of ways which should be apparent to those skilled in the art. The first handle member 23 preferably includes a groove 25 therein for allowing it to be removably attached to the saw member 15. That is, the groove 25 preferably includes an offset portion 27 for securely gripping the first end 17 of the saw member 15 when the first end 17 of the saw member 15 is passed therethrough and tension is applied thereto. The first handle member 23 may be constructed of wood, plastic or the like. The saw means 11 also includes a second handle member 29 fixedly attached to the second end 19 of the saw member 15. The second handle member 29 may be fixedly attached to the second end 19 of the saw member 15 in any number of ways which should be apparent to those skilled in the art. Preferably, the second handle member 29 includes a bar-like portion 31 and a ring member 33 which passes through an aperture 35 in the bar-like portion 31. The second end 19 of the saw member 15 is preferably provided with a loop-like portion 37 through which the ring member 33 of the second handle member 29 passes through to fixedly attach the second handle member 29 to the second end 19 of the saw member 15. It should be noted that the bar-like portion 31 of the second handle member 29 may be constructed of wood, metal, plastic or the like.

Figure 5:
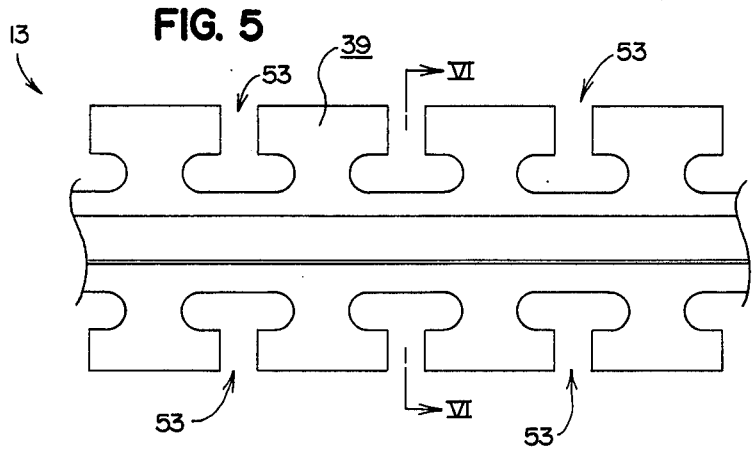
FIG. 5 is a front view of the strip member of the guide means of the present invention.
Figure 6:
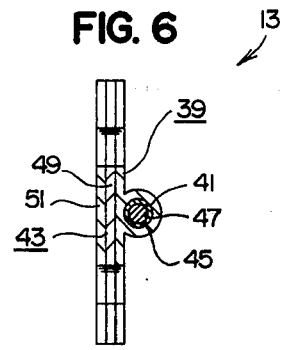
FIG. 6 is a sectional view of the guide means of the present invention as taken on line VI—VI of FIG. 5.

The guide means 13 includes a flexible elongated strip member 39 having an elongated aperture 41 along the longitudinal axis thereof and having attachment means 43 on one side thereof for selectively attaching the strip member 39 to the body member before the cast is applied thereto. The guide means 13 may include a flexible elongated conduit member 45 fixedly positioned in the elongated aperture 41 of the strip member 39. In addition, the guide means 13 may be provided with a flexible elongated core 47 removably positioned therein. The core 47 is preferably constructed of a noncollapsible material to prevent the elongated aperture 41 from collapsing. The attachment means 43 may include a preferably pressure-sensitive adhesive portion 49 affixed to one side of the strip member 39 for selectively attaching the strip member 39 to the body member before the cast is applied thereto. In addition, the attachment means 43 preferably includes a nonadhesive backing member 51 removably positioned on the adhesive portion 49 to prevent accidental attachment of the strip member 39. The strip member 39 is preferably provided with a plurality of spaced slits 53 along each longitudinal edge thereof for increasing the flexibility of the strip member 39. Each of the plurality of spaced slits 53 is preferably T-shaped as clearly shown in FIG. 5 for maximizing the flexibility of the strip member 39 and for other reasons which will hereinafter become apparent.

The preferred method of removing a cast from a patient's body member B begins at the time the cast C is being applied to the body member B. The first step in applying a cast C to a patient's body member B is typically the wrapping of the body member B with padding P such as gauze, stockinette or the like (see FIG. 7).

Figure 7:
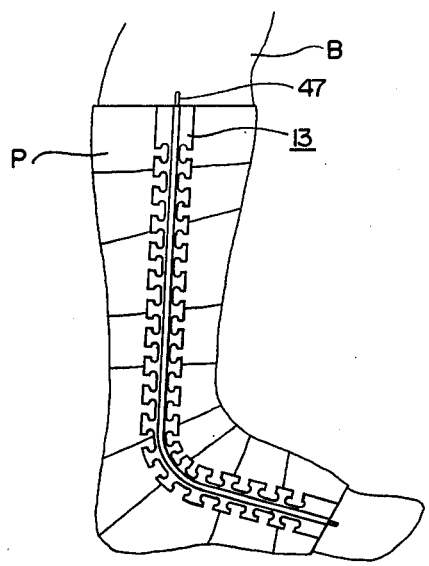
FIG. 7 is a somewhat diagrammatic view of a body member showing padding being wrapped therearound and showing the guide means of the present invention attached thereto.
Figure 8:
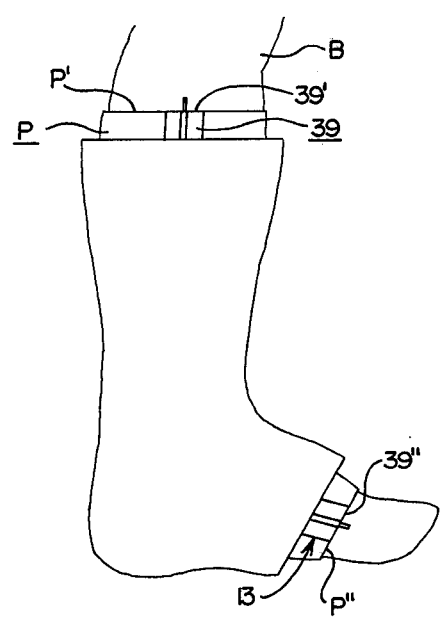
FIG. 8 is a view somewhat similar to FIG. 7 but showing a cast being applied over the padding and guide means.
Figure 9:
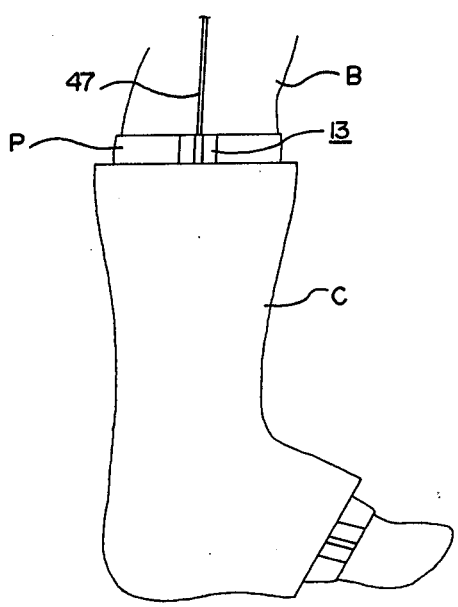
FIG. 9 is a view somewhat similar to FIG. 8 but showing the core of the guide means being removed therefrom.
Figure 10:
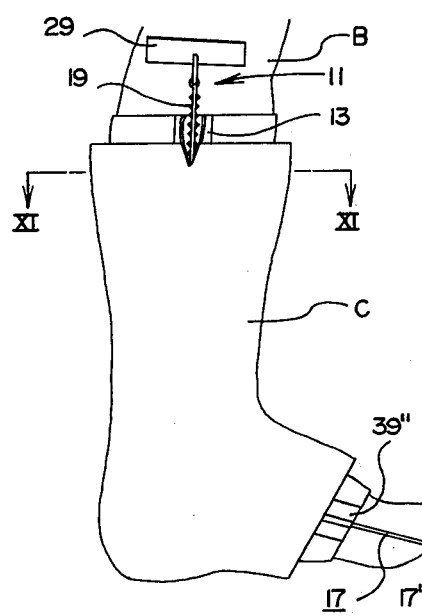
FIG. 10 is a view somewhat similar to FIG. 9 but showing the saw means of the present invention inserted in the guide mean and cutting through the cast.
Figure 11:
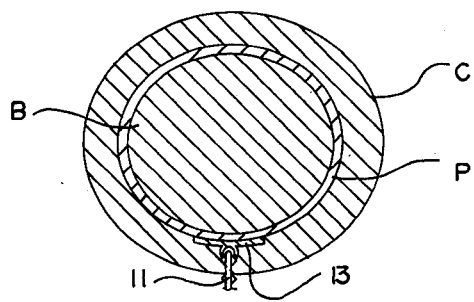
FIG. 11 is a sectional view as taken on line XI—XI of FIG. 10.

After the padding P has been applied to the body member B, the guide means 13 is attached thereto over the padding P (see FIG. 7). More specifically, the strip member 39 is first cut to the desired length, the nonadhesive backing portion 51 is removed from the adhesive portion 49 of the strip member 39, and the strip member 39 is attached to the body portion B over the padding P by way of the adhesive portion 49. It should be noted that the strip member 39 is bent as it is attached to the body member B to follow all the curves in the body member B. The cast C is then applied to the body member B over the padding P and the guide means 13 (see FIG. 8). Preferably, the cast C is applied so that the opposite ends P',P" of the padding and the opposite ends 39', 39" of the strip member 39 extend past the respective ends of the cast C (see FIG. 8). The opposite ends P', P" of the padding P may be turned back upon the cast C and made integral with the cast C in a manner well known to those skilled in the art. The slits 53 in the strip member 39, in addition to allowing the strip member 39 to be easily bent to follow all of the curves of the body member B, allow a more effective bond between the strip member 39 and the cast C than would be possible if the strip member 39 was not provided with such slits. After the cast C has remained upon the body member B for a sufficient period of time, the core 47 is removed from the elongated aperture 41 of the strip member 39 (see FIG. 9). Next, the smooth first end 17 of the saw member 15 is inserted through the conduit 45 so that a portion 17' of the first end 17 of the saw member 15 extends past the end portion 39" of the strip member 39. The first handle 23 is then attached to the portion 17' of the first end 17 of the saw member 15 that extends past the end portion 39" of the strip member 39 (see FIG. 10). The saw member 15 is then moved back and forth within the conduit 45 in the elongated aperture 41 of the strip member 39 by alternately pulling and relinquishing alternate ones of the first and second handle members 23, 29 thereby causing the plurality of saw teeth 21 of the second end 19 of the saw member 15 to cut through the conduit 45 (if one is provided), the wall of the elongated aperture 41 of the strip member 39, and the cast C. It should be noted that by dividing the saw member 15 into first and second ends 17, 19 with the first end 17 being smooth allows the cut through the cast C to be very accurately made. That is, by only having saw teeth on one end of the saw member 15, the cut through the cast C can be controlled so as to make the cut progressively from one end of the cast C to the other.

Although the invention has been described and illustrated with respect to a preferred embodiment thereof, it is not to be so limited since changes and modifications may be made therein which are within the full intended scope of the invention.

I claim:

1. Means for removing a cast from a body member, said means for removing a cast comprising a saw means for cutting through the cast, said saw means including a flexible elongated saw member having a first end and a second end, said saw member including a plurality of saw teeth provided only adjacent said second end thereof and being substantially smooth along its entire length except for said second end thereof, said saw means including a first handle member removably attached to said first end of said saw member and including a second handle member fixedly attached to said second end of said saw member.

2. The means for removing a cast of claim 1 in which said saw means consist of an elongated length of woven wire and in which said plurality of saw teeth of said second end of said saw member are formed by varying the pitch of alternating strands of said woven wire.

3. The means for removing a cast of claim 1 in which is included guide means for guiding said saw member of said saw means, said guide means including a flexible elongated strip member having an elongated aperture along the longitudinal axis thereof and having attachment means on one side thereof for selectively attaching said strip member to the body member before the cast is applied thereto.

4. The means for removing a cast of claim 3 in which said guide means includes a flexible elongated conduit member fixedly positioned in said elongated aperture of said strip member of said guide means.

5. The means for removing a cast of claim 4 in which said conduit member is provided with a flexible elongated core removably positioned therein, said core being noncollapsible.

6. The means for removing a cast of claim 3 in which said attachment means of said guide means includes an adhesive portion affixed to one side of said strip member for selectively attaching said strip member to the body member before the cast is applied thereto.

7. The means for removing a cast of claim 6 in which said attachment means includes a nonadhesive backing member removably positioned on said adhesive portion of said attachment means to prevent accidental attachment of said strip member.

8. The means for removing a cast of claim 3 in which said strip member is provided with a plurality of spaced slits along each longitudinal edge thereof for increasing the flexibility of said strip member.

9. Means for removing a cast from body member, said means for removing a cast comprising:
   a. guide means including a flexible elongated strip member having an elongated aperture along the longitudinal axis thereof and having attachment means on one side thereof, said attachment means including an adhesive portion affixed to one side of said strip means for selectively attaching said strip member to the body member before the cast is applied thereto, said guide means including a flexible elongated conduit member fixedly positioned in said elongated aperture of said strip member, said conduit member being provided with a flexible elongated core removably positioned therein, said core being noncollapsible; and
   b. saw means for cutting through the cast, said saw means including a flexible elongated saw member for selectively extending through said elongated aperture of said strip member of said guide means, said saw member including a first end and a second end, said saw member including a plurality of saw teeth provided only on said second end thereof and being substantially smooth along its entire length except for said second end thereof, said saw means including a first handle member removably attached to said first end of said saw member and including a second handle member fixedly attached to said second end of said saw member.

10. A method of removing a cast from a body member, said method comprising:
    a. attaching a flexible elongated strip member having an elongated aperture along the longitudinal axis thereof to the body member before the cast is applied thereto;
    b. inserting a first end of a flexible elongated saw member through said elongated aperture in said strip member after the cast is applied to the body member over said strip member so that a portion of said first end of said saw member extends past said strip member, said saw member including a second end and including a plurality of saw teeth provided only on said second end thereof and being substantially smooth along its entire length except for said second end thereof, said saw member including a handle member fixedly attached to said second end thereof;
    c. attaching a handle member to said portion of said smooth first end of said saw member that extends past said strip member; and
    d. moving said saw member back and forth within said elongated aperture in said strip member by alternating pulling and relinquishing alternate ones of said handle members thereby causing said plurality of saw teeth of said second end of said saw member to cut through the cast.

* * * * *